United States Patent
Jenkins et al.

[11] Patent Number: 5,919,143
[45] Date of Patent: Jul. 6, 1999

[54] APPARATUS AND METHOD FOR ANALYSIS OF ACOUSTIC REFLECTANCE AND THERMAL RADIATION OF AN EAR

[75] Inventors: Geoffrey Jenkins, Wellesley; Sandra Kimball, Boston, both of Mass.

[73] Assignee: MDI Instruments, Inc., Woburn, Mass.

[21] Appl. No.: 09/006,543

[22] Filed: Jan. 12, 1998

[51] Int. Cl.[6] .................................................. A61B 5/103
[52] U.S. Cl. ........................................ 600/549; 600/559
[58] Field of Search ................................ 600/549, 559; 73/585

[56] References Cited

U.S. PATENT DOCUMENTS

| | | | |
|---|---|---|---|
| 4,601,295 | 7/1986 | Teele | 600/559 |
| 5,199,436 | 4/1993 | Pawpei et al. | 600/546 |
| 5,368,038 | 11/1994 | Fraden | 600/546 |
| 5,651,371 | 7/1997 | Keefe | 600/559 |

*Primary Examiner*—Max Hindenburg
*Attorney, Agent, or Firm*—Wolf, Greenfield & Sacks, P.C.

[57] ABSTRACT

A radiation thermometer and acoustic reflectometer are combined in the same device. The combined instrumentation can be used to improve alignment between a device and the tympanic membrane, thus improving the accuracy of measurements. In addition, the device can provide diagnostic information based on both the measured temperature and the determined likelihood that fluid is present in the middle of the ear, to indicate the risk of an ear infection. The medical instrument analyzes an ear of a subject, using an acoustic reflectometer and a radiation thermometer. The acoustic reflectometer includes an acoustic transducer for generating acoustic waves at a plurality of frequencies and a microphone for receiving an acoustic signal corresponding to acoustic signals reflected from the ear to provide an output signal. The radiation sensor detects thermal radiation from the ear and provides a signal indicative thereof. The device coordinates measurements by the acoustic reflectometer and radiation sensor to provide an output indicative of a condition of the ear. The medical instrument may indicate to the user when both an elevated temperature and fluid are detected in the ear to provide an indication of a risk of ear infection.

7 Claims, 8 Drawing Sheets

|  | TEMP < 99° | TEMP 99° - 100° | TEMP > 100° |
|---|---|---|---|
| S.G. ANGLE > 95° | a WELL | b LOW TEMP NO FLUID | c HI TEMP NO FLUID |
| S.G. ANGLE 70° - 95° | d OME | e AOM | f AOM |
| S.G. ANGLE < 70° | g OME | h AOM | i AOM |

Fig. 10

| Ear Infection AOM | |
|---|---|
| Hi | f,h,i |
| Mod. | e,g |
| Low | a,b,c,d |

Fig. 11

| Fluid OME | |
|---|---|
| Hi | g,h,i |
| Mod. | d,e,f |
| Low | a,b,c |

Fig. 12

APPARATUS AND METHOD FOR ANALYSIS OF ACOUSTIC REFLECTANCE AND THERMAL RADIATION OF AN EAR

FIELD OF THE INVENTION

The present invention is related to devices and methods for analyzing conditions of an ear, such as temperature of the inner ear, infection and presence of fluid in the middle ear.

BACKGROUND OF THE INVENTION

One device that has become generally accepted and is commonly used by physicians and other health care professionals is known as a radiation thermometer, or infrared thermometer. Such devices are commercially available from Thermoscan, Inc. of San Diego, Calif. Devices of this type are described, for example, in U.S. Pat. Nos. 5,368,038 (Fraden), 4,797,840 (Fraden), 4,479,931 (Mooradian), 5,127,742 (Fraden), 5,178,464 (Fraden), 5,626,147 (Lackey), 4,895,164 (Wood), and 5,199,436 (Pompei). A radiation thermometer noninvasively detects thermal radiation from the tympanic membrane in order to determine the body temperature of the patient. A temperature reading made with this device may vary depending on the angle and depth of placement of the tip of the device with respect to the ear canal. In particular, the geometric relationship between the sensor and the tympanic membrane influences the ultimate reading by the sensor in operation. The field of view of the device, when detecting thermal radiation also affects the temperature reading. The technology described in U.S. Pat. No. 5,626,147 (Lackey) seeks to solve these problems by using a sensor geometry which has wide and narrow fields of view and a look-up table with corrective values to provide an output indicative of the body temperature.

Similar problems exist in measuring acoustic reflectance of an ear. Acoustic reflectance is measured by measuring sound waves emitted from the ear in response to a stimulus applied to the ear. The measured reflectance may be analyzed to determine the likelihood that fluid is present in the middle ear. Acoustic reflectometers are described, for example, in U.S. Pat. Nos. 4,601,295 (Teele), 4,459,966 (Teele), and published PCT Publication WO96/23293 (Combs et al.), all of which are assigned to MDI Instruments, Inc., of Woburn, Mass. Products are commercially available from MDI Instruments, Inc., under the trademarks "EARCHECK" and "EARCHECK PRO." U.S. Pat. Nos. 5,594,174 and 5,651,371 also describe a device for measuring acoustic reflectance in a manner that permits the incident and reflected acoustic signals to be separately measured. Measurements made using an acoustic reflectometer also may be affected by line of sight measurements from the tip of the device to the tympanic membrane. While the aforementioned PCT publication describes a device in which the output is substantially independent of the line of sight, the device primarily determines the likelihood that fluid is present in the ear. The device also can measure conductive hearing loss. However, in the detection of acute otitis media or severe ear infection, fluid is only one factor in a diagnosis.

SUMMARY OF THE INVENTION

The present invention involves combining radiation thermometry and acoustic reflectometry in the same device. The combined instrumentation can be used to improve alignment between a device and the tympanic membrane, thus improving the accuracy of measurements. In addition, the device can provide diagnostic information based on both the measured temperature and the determined likelihood that fluid is present in the middle of the ear, to indicate the risk of an ear infection.

Accordingly, in one aspect a medical instrument for analyzing an ear of a subject includes an acoustic reflectometer and a radiation thermometer. The acoustic reflectometer includes an acoustic transducer for generating acoustic waves at a plurality of frequencies and a microphone for receiving an acoustic signal corresponding to acoustic signals reflected from the ear to provide an output signal. The radiation sensor detects thermal radiation from the ear and provides a signal indicative thereof. The device coordinates measurements by the acoustic reflectometer and radiation sensor to provide an output indicative of a condition of the ear.

In another aspect, a process for analyzing an ear includes detecting thermal radiation and measuring acoustic reflectance from an ear.

When both an elevated temperature and fluid are detected in the ear, and indication of a risk of ear infection may be provided.

BRIEF DESCRIPTION OF THE DRAWINGS

In the drawings:

FIG. 10 is an example look-up table for providing a diagnosis based on both temperature and a measure of acoustic reflectance;

FIG. 11 is an example table for displaying the likelihood of an ear infection based on the results obtained from the look-up table of FIG. 10; and FIG. 12 is an example table for displaying the probability of fluid being present in the middle ear based on the results obtained from the look-up table of FIG. 10.

DETAILED DESCRIPTION

The present invention will be more completely understood through the following detailed description which should be read in conjunction with the attached drawing in which similar reference numbers indicate similar structures. All references cited herein are hereby incorporated by reference.

The present invention is a device that measures both thermal radiation and acoustic reflectance of the ear. Both body temperature and the likelihood that fluid is present in the middle of the ear may be determined. The output for one of the measurements, e.g., the radiation, can be used to align the device with the tympanic membrane, thus improving the other measurement, e.g., the acoustic reflectance. In addition, the combined measurements may be used together to enhance diagnosis of ear conditions. In particular, an elevated temperature with the presence of fluid indicates a high risk of ear infection.

Figure 1:
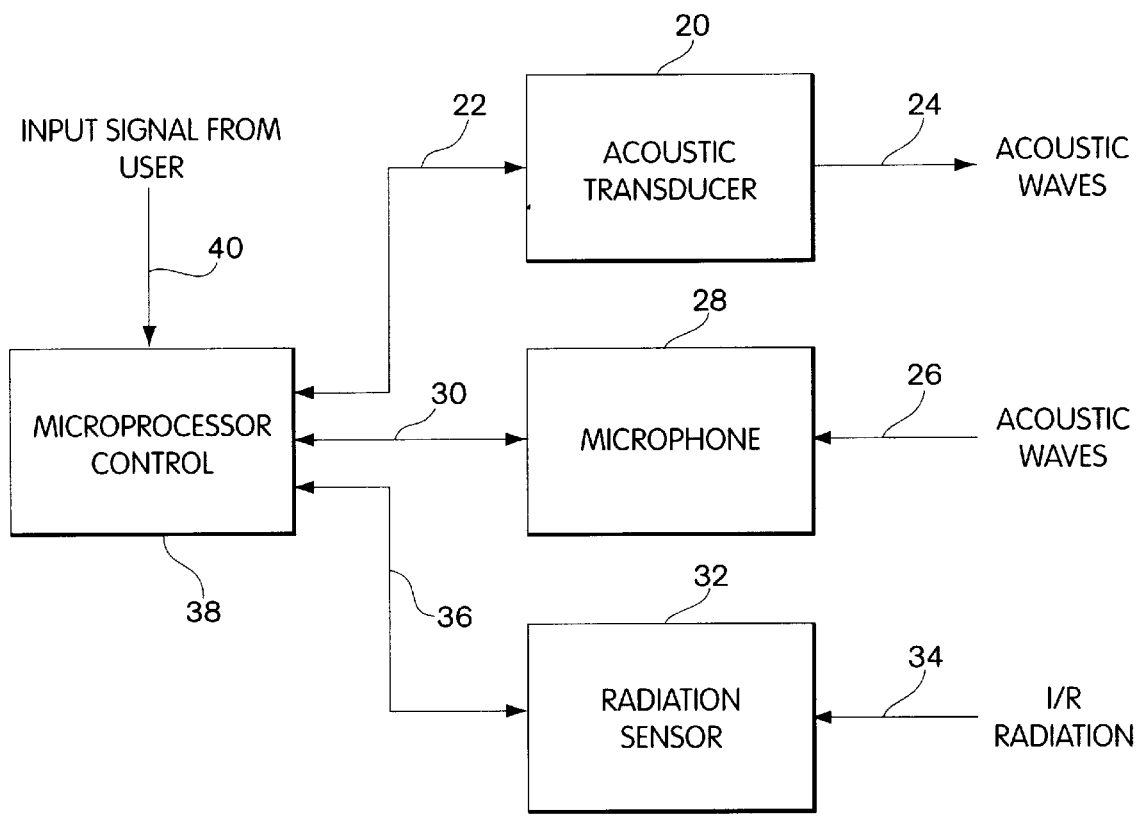
FIG. 1 is a block diagram of the electronic components of the combined acoustic reflectometer and radiation sensor of the invention.

FIG. 1 illustrates a circuit diagram for a system in one embodiment of the present invention. The system includes an acoustic transducer 20 which, in response to inputs 22 from a microprocessor controller 38 emits acoustic waves 24 into, for example, the ear canal. These incident acoustic waves 24 and reflected acoustic waves 26 are received by a microphone 28. In some embodiments, it is possible to separate the reflected acoustic waves from the incident acoustic waves. The microphone 28 provides this measurement to the microprocessor controller 38 as indicated at 30. A radiation sensor 32 detects infrared radiation 34 from the ear and provides signal 36 to the microprocessor controller 38. The microprocessor controller 38 receives an input signal 40 from the user which indicates whether a reading should be taken. The microprocessor controller 38 then controls the acoustic transducer, microphone and radiation sensor to obtain data. The microprocessor controller 38 processes the data to provide results for display to the user, for example, according to the process described in FIG. 9 below.

The combination of the acoustic transducer 20 and microphone 28 to provide the output acoustic signal to the ear may be implemented in many ways, such as those described in U.S. Pat. Nos. 4,459,966, 4,601,295, 5,594,174, 5,651,371, and PCT application No. WO96/23293, cited above and hereby incorporated by reference.

Figure 2:
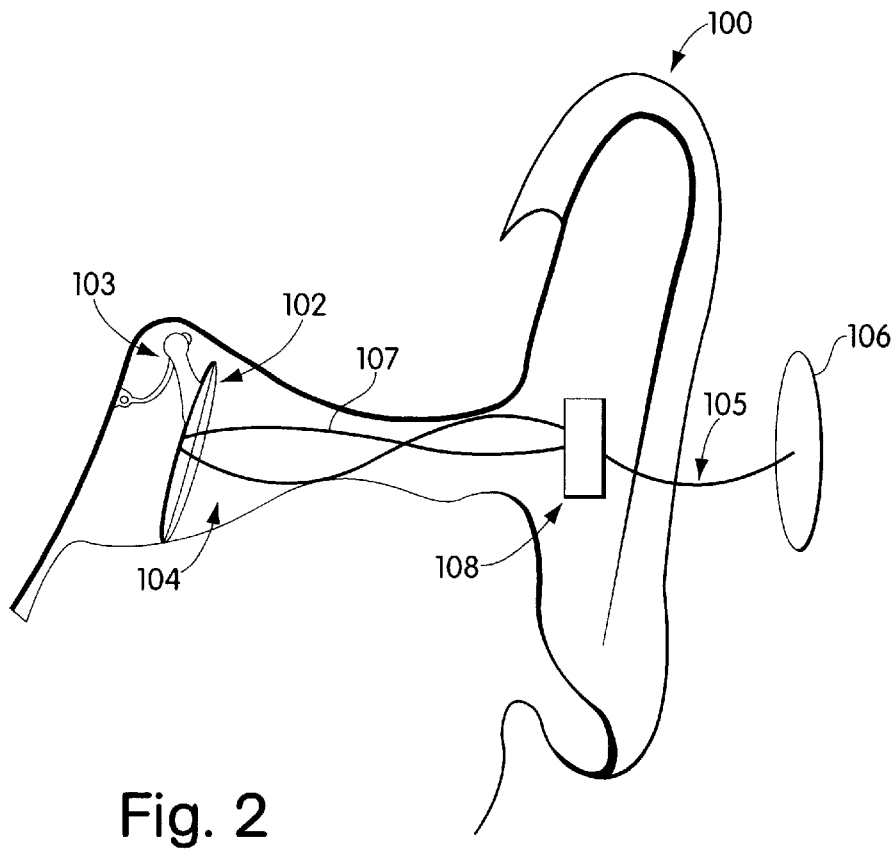
FIG. 2 is diagram illustrating acoustic reflectance of a healthy ear.

The process of measuring acoustic reflectance of an ear, in one embodiment of the invention, will first be described in connection with FIGS. 2–5. FIG. 2 shows a typical ear 100 having a tympanic membrane (an ear drum) 102, an ear canal 104, and middle ear 103. To measure acoustic reflectance, a low amplitude tone at a given frequency, indicated by line 105, is generated by an acoustic transducer, shown schematically at 106. The acoustic transducer generates sound waves for several frequencies, typically in the range of 500 Hertz to 20 kiloHertz, or more particularly, 1.8 kiloHertz to 4.4 kiloHertz. The low amplitude sound wave enters the ear canal and is incident on the ear drum 102. This sound wave is absorbed in part and reflected in part by the ear structures, including the tympanic membrane, oscicles, middle ear cleft and other components of the middle ear. The amplitude and phase of the reflected sound waves from these components are a function of the test frequency used and the complex acoustic impedance of the ear structures. In a healthy ear, some minimal reflection from the tympanic membrane and middle ear is expected. The complex acoustic impedance of the middle ear, in turn, depends very strongly on the conditions within the middle ear, and in particular on whether there is an effusion, such as fluid or abnormal pressure, in the middle ear. The vibration of a normal ear drum absorbs approximately half of the incident waves, resulting in weak reflected waves indicated by a line 107. A microphone 108 receives both the incident wave 105, the reflected wave 107 and reflected waves from ear components and as a result obtains a vector sum of the values. In other embodiments, the reflected sound may be separated from the incident sound.

Figure 3:
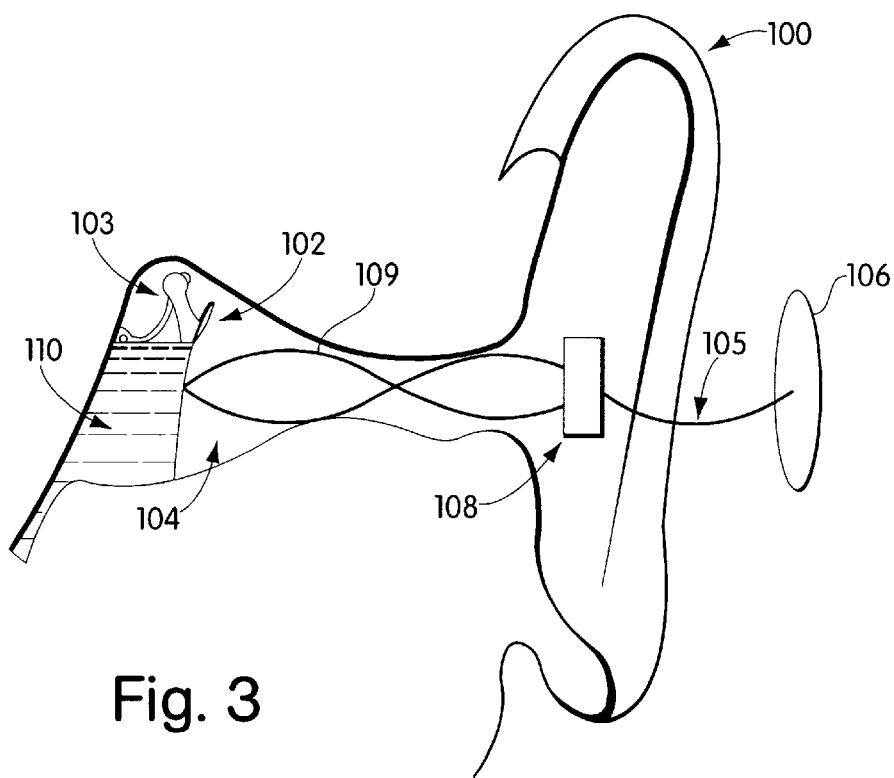
FIG. 3 illustrates acoustic reflectance and an ear having fluid behind the tympanic membrane.

Referring now to FIG. 3, an ear 100 is shown to have effusion 110. The middle ear effusion limits ear drum vibration, causing large reflected waves to have a larger amplitude as indicated at 109. The envelope of a vector sum of incident waves 105 and reflected waves 109, herein called an acoustic reflectance curve, has a null at the quarter wave length points.

The shape of a region of the acoustic reflectance curve, defined by at least two points on the curve, is measured electronically to obtain an indicator of ear condition which is substantially independent of the line of sight between the sound source and the tympanic membrane. The indicator may be a measure of the rate of change of the acoustic reflectance with respect to a change in frequency on either or both sides of the null, around the null, of other regions of the curve or of the entire curve. The area around the null is where the curve has a significant negative slope, defining entry into the null, to a point just before the null, and after the null, where the curve has a significant positive slope, defining the exit of the null. The null typically occurs near the resonance frequency of the ear. The significance of this measurement will now be described.

As the sound wave incident to the tympanic membrane approaches a frequency where its quarter waves are coincident, the amplitude of the vector sum of the reflected sound waves and the incident sound waves approaches a null. Generally speaking, normally conducting ear drums without fluid or abnormal pressure in the middle ear demonstrate a relatively shallow acoustic null. Conversely, fluid or abnormal pressure in ears causes a stronger reflection and therefore a deeper acoustic null. The depth of this null is dependent, however, on the line of sight to the eardrum. It has been discovered, however, that the rate of change of the acoustic reflectance between the entry into the null and the exit from the null is steeper for ears having middle ear fluid or pressure than for healthy ears. It was further discovered that differences in this rate of change due to changes in line of sight have less of an impact on the indication of the presence of an effusion or abnormal pressure.

Eardrums that are free to vibrate with the incident sound wave (i.e., healthy) produce not only a less deep null but also a less steep slope at frequencies around the null and thus a smaller spectral gradient. The restrained motion produces lower reflectance values relative to the peak null at nearby frequencies and therefore an apparent lower slope.

When the eardrum motion is restrained (i.e., the ear is not healthy), the slope around the null is steeper. Because acoustic reflectance is related to the complex acoustic impedance of the tympanic membrane, the measure of its rate of change with respect to frequency input is analogous to measuring the "Q" of an electrical circuit. Thus, restraining the ear drum results in both a higher acoustic impedance and a sharper "Q." The "Q" is relatively constant for a given impedance regardless of variations in the amount of energy incident due to line of sight limitations.

Figure 4:
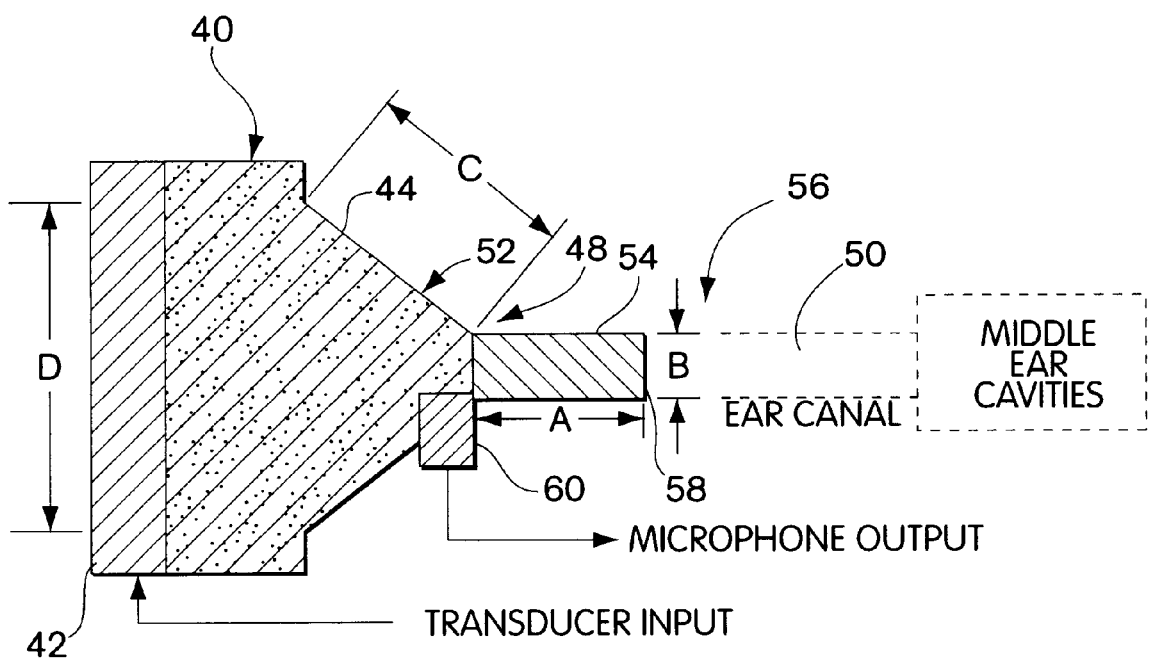
FIG. 4 is a diagram of test head that may be used for acoustic reflectance.

A device for one embodiment of the invention will now be described. FIG. 4 is a cross sectional diagram of a test head for an instrument in accordance with the invention. The test head 40 includes a transducer 42 that creates a sound field in sound cavity 44. Sound in the cavity 44 is channeled through probe 48 to the vicinity of the ear canal 50. The probe has a funnel-shaped section 52 and an optional linear section 54. The dimensions of section 54 may be chosen to match the dimensions of the typical healthy ear canal under test. This thereby matches the impedance of the probe tip and the typical ear canal. For children's ears, length A of the linear portion 54 of the probe preferably is equal to approximately 1 cm and inner diameter B of the same section should be in the range of approximately 0.25 to 0.75 cm. Similarly, good results are obtained when length C along the side of funnel-shaped section 52 of the probe is about 5 cm and the approximate outer diameter D of the large end of the probe which is in contact with the sound cavity wall is approximately 7 cm. With appropriate compensation, tips with other exit diameters may be used. The probe extension does not need to be inserted into the ear canal. In practice, there may be a narrow gap 56 between the test head probe tip 58 and the entrance to the ear canal 50. Control of this gap may be facilitated by a response rubber spacer (not shown) attached at the end of probe tip 58.

The incident sound wave created by transducer 42 in the test head emanates from the test head at the tip 58 of the probe 48 and enters the ear canal 50. Thereafter, a portion of the incident wave is reflected by structures of the ear. Minimal reflection from a healthy ear can be suppressed by suitable selection of the inner probe tip diameter, e.g., by enlarging it to 1.0 cm for children.

Portions of the reflected waves enter at tip 58 into the hollow linear portion 54 of the test head. The microphone 60 is located within the test probe 48 at the junction of the linear portion of 54 and the funnel-shaped section 52. As a result, the microphone 24, in effect, measures the net sound pressure at this point; this net sound pressure is the vector sum of the incident and reflected signals. In order to reduce internal sound reflection and resonances within the test head, the sound cavity 44 may be filled with acoustic absorbing materials.

In other embodiments, a transfer function describing the acoustic characteristics of the ear may be determined and used as the basis for a diagnosis.

Figure 5:
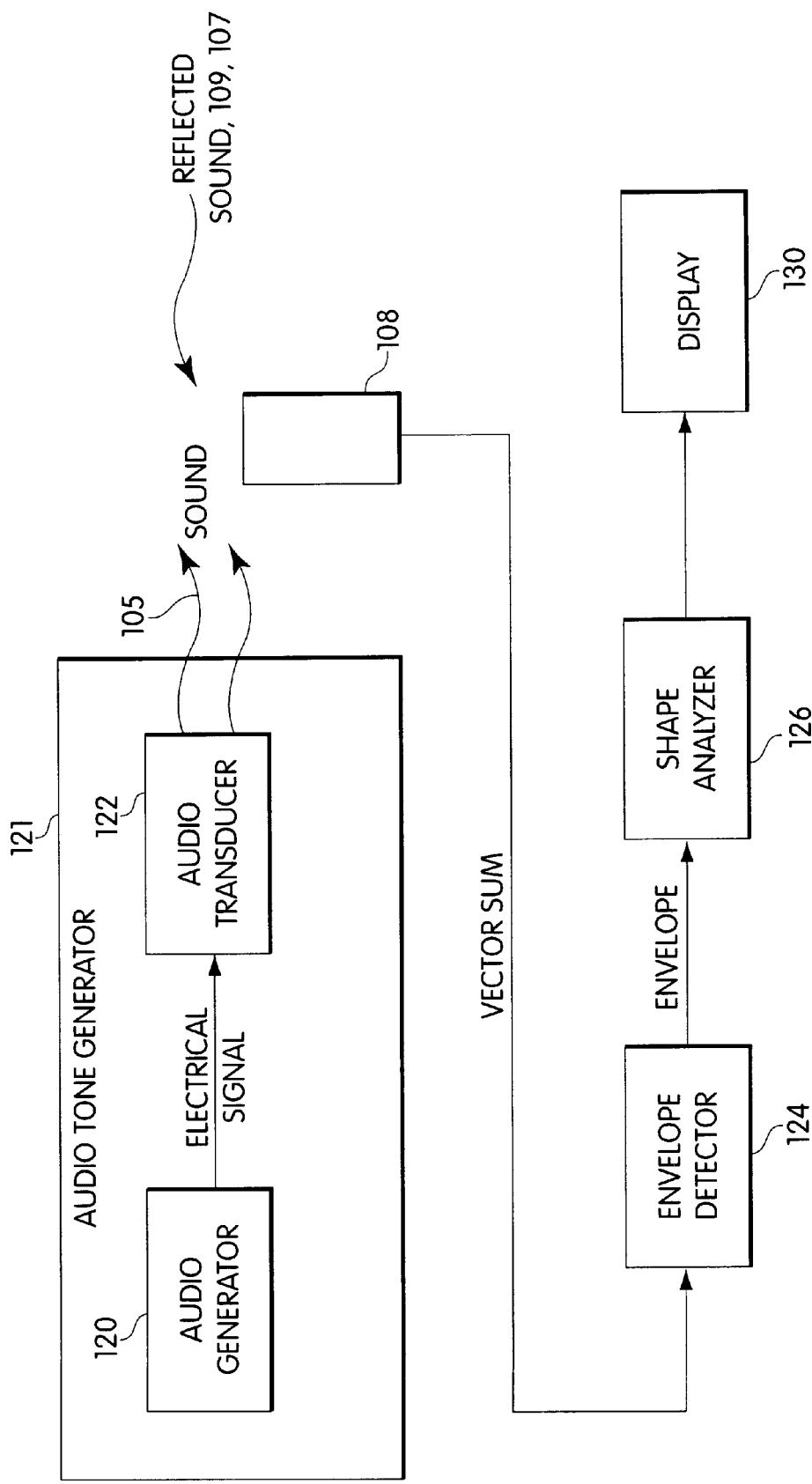
FIG. 5 is a block diagram describing an electronic circuit for measuring acoustic reflectance.

Having now described the general principles for measuring acoustic reflectance, and a suitable test head for use in an acoustic reflectometer, electronic circuitry suitable for an embodiment of the invention will now be described in connection with FIG. 5. FIG. 5 is a general block diagram of a device in accordance with the invention, including its electrical and mechanical components. The components of this circuit may be implemented using a microprocessor, except for the display, acoustic transducer and microphone. An analog implementation also may be made. In FIG. 5, an audio tone generator 121 includes an audio generator 120, which produces an electrical signal which is applied to an audio transducer 122 (such as transducer 42 in the test head of FIG. 4). The audio transducer, in response to the electrical signal, generates a low level acoustic sound wave (105 in FIGS. 2 and 3) which is applied to the outer ear canal. The audio transducer 122 may be an electronic earphone, electromagnetic earphone, or other type of transducer. The transducer may be a small loudspeaker such as used in high fidelity sound headsets.

A portion of the incident sound wave is reflected by ear structures as described above. In this embodiment, these reflected waves are summed with an incident wave by microphone 108 (such as microphone 24 of the test head of FIG. 4). The microphone may be a condenser microphone, an electrostatic microphone or other kind of microphone. In this embodiment, the signal output by the microphone represents the vector sum of the incident wave and the reflected sound waves, having a voltage which is inversely proportional to the amplitude of the reflected waves.

An envelope detector 124 converts the vector sum represented by the signal output by the microphone to an envelope signal represented by a voltage which varies with the frequency of the incident wave. The envelope detector 124 may be implemented as a peak value envelope detector, a root-mean square (RMS) voltage detector, or analog-to-digital converter, such as part of a suitably programmed microprocessor. In one aspect of the invention described in more detail below, the envelope is detected using information about the frequency spectrum of the vector sum. The envelope so detected is called the acoustic reflectance curve.

A shape analyzer 126 electronically measures the shape of a region of the acoustic reflectance curve to obtain an indicator of ear condition which is substantially independent of the line of sight form a sound source to the tympanic membrane. This information may be one or more measures of the shape of the envelope including a measure of the rate of change of acoustic reflectance with respect to a change in frequency around the null, on either side of the null or on a region of the curve or of the entire curve. This measure, for example, may be an angle, gradient, slope, width, or other measure of the shape of the acoustic reflectance curve determined in a manner to be described below. This information is then displayed in a suitable format by display section 130.

In FIG. 5, a memory (not shown) may be added to store results of processing of one acoustic reflectance curve. With such a memory, the circuit may be operated to perform automatically a number of tests sequentially on the ear. The best results for the sequence of tests may be kept and the others may be discarded. For example, the best results could be defined as the measurement of the shape of the acoustic reflectance curve having the deepest null value. In this manner, a user of the device may attempt to get the best result with little effort. The use of this memory is described below in more detail in connection with FIG. 9.

The radiation sensor may be implemented in many ways to provide a reading of temperature to the microprocessor control, for example, as shown in U.S. Pat. Nos. 5,626,147; 5,368,038; 5,199,436; 5,178,464; 5,127,742; 4,797,840; and 4,479,931, cited above and hereby incorporated by reference.

One embodiment of the radiation thermometer uses a sensor system that compensates for different ear canal placement geometries by creating an IR signal collected via both wide and narrow fields of view. By using IR information that is responsive to a wide field of view in conjunction with information from a narrow field of view, the errors in temperature reading occasioned by the vagaries in probe positioning in the ear can be compensated by appropriately programmed signal adjustment. Specially, the signal processor integrated with the sensor, weights the input from both sources and using a look-up table, applies corrective values to give an accurate and repeatable temperature measurement. This value also is indicative of alignment of the device with the ear.

Figure 6:
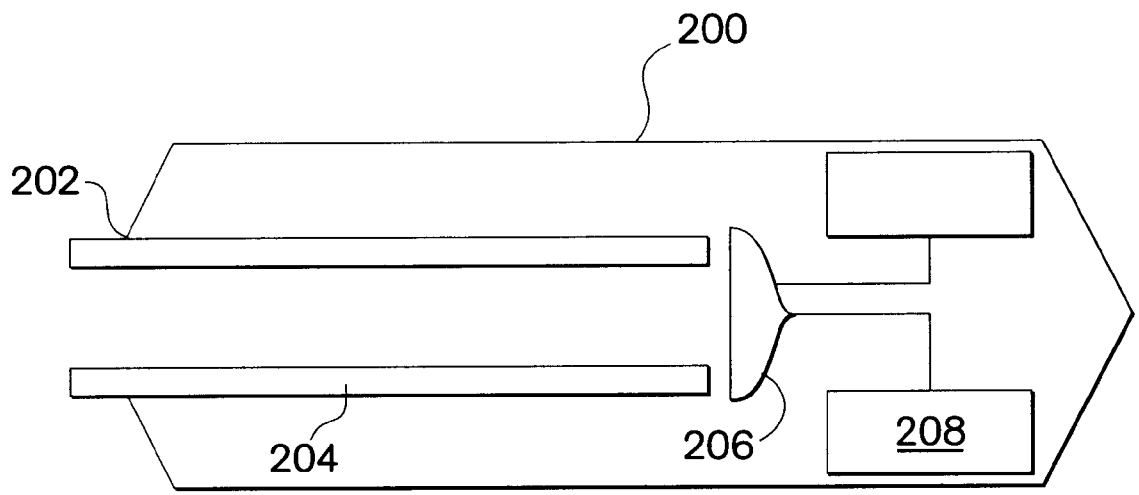
FIG. 6 is a diagram illustrating a radiation thermometer.

With the foregoing overview in mind, attention is directed to FIG. 6 which provides a simplified diagram of the salient elements in an IR thermometer. In this illustrative diagram, the thermometer device provides a housing 200 for containment of the operative elements of the device. The housing has a terminus end at which an IR receiving opening 202 is positioned to feed incoming radiation to a wave guide 204. There are a variety of possible wave guides available for use that offer different performance characteristics in terms of distortion and prices, ranging from smooth gold-plated tubes to fiber optic bundles. In functional terms, the wave guide is designed to collect and pass incoming radiation undisturbed to IR sensor 206. Again, there are several choices in sensor systems, including thermopile types and pyroelectric elements. In the embodiment to be described, the sensor is a pyroelectric sensor, which uses "matched pairs" to cancel out signal contributions intrinsic with the pyroelectric elements.

Continuing with FIG. 6, the sensor 206 is connected to processor 208 for converting the IR data into a high quality temperature reading as well be described in more detail below. In the context of the present invention, the sensor design has been modified to create signals for both wide and narrow fields of view. This is accomplished by creating two or more sensors, each reporting separately to the processor information on radiation.

Figure 7:
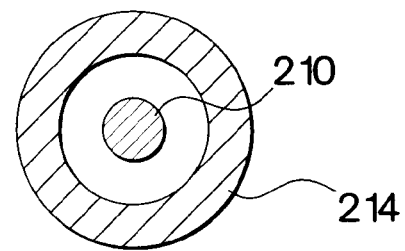
FIG. 7 is a diagram illustrating two sensors for use with radiation thermometry.

The sensor geometry capable of this is depicted in FIG. 7. More specifically, the sensor 206 of FIG. 5 is, in fact, two separate sensors, 210 and 212, each connected to the processor 208. The first sensor 210 is relatively smaller and concentric to the center line of the wave guide 204, thus providing a narrow field of view. The outer sensor 212, on the other hand, is somewhat larger and positioned outside the perimeter of the wave guide, thereby providing a relatively wider field of view.

This kind of radiation thermometer, or other type, may be used in combination with an acoustic reflectance. The uncorrected temperature or output of two radiation sensors may be used to provide alignment for acoustic measurement as will now be described.

Figure 8:
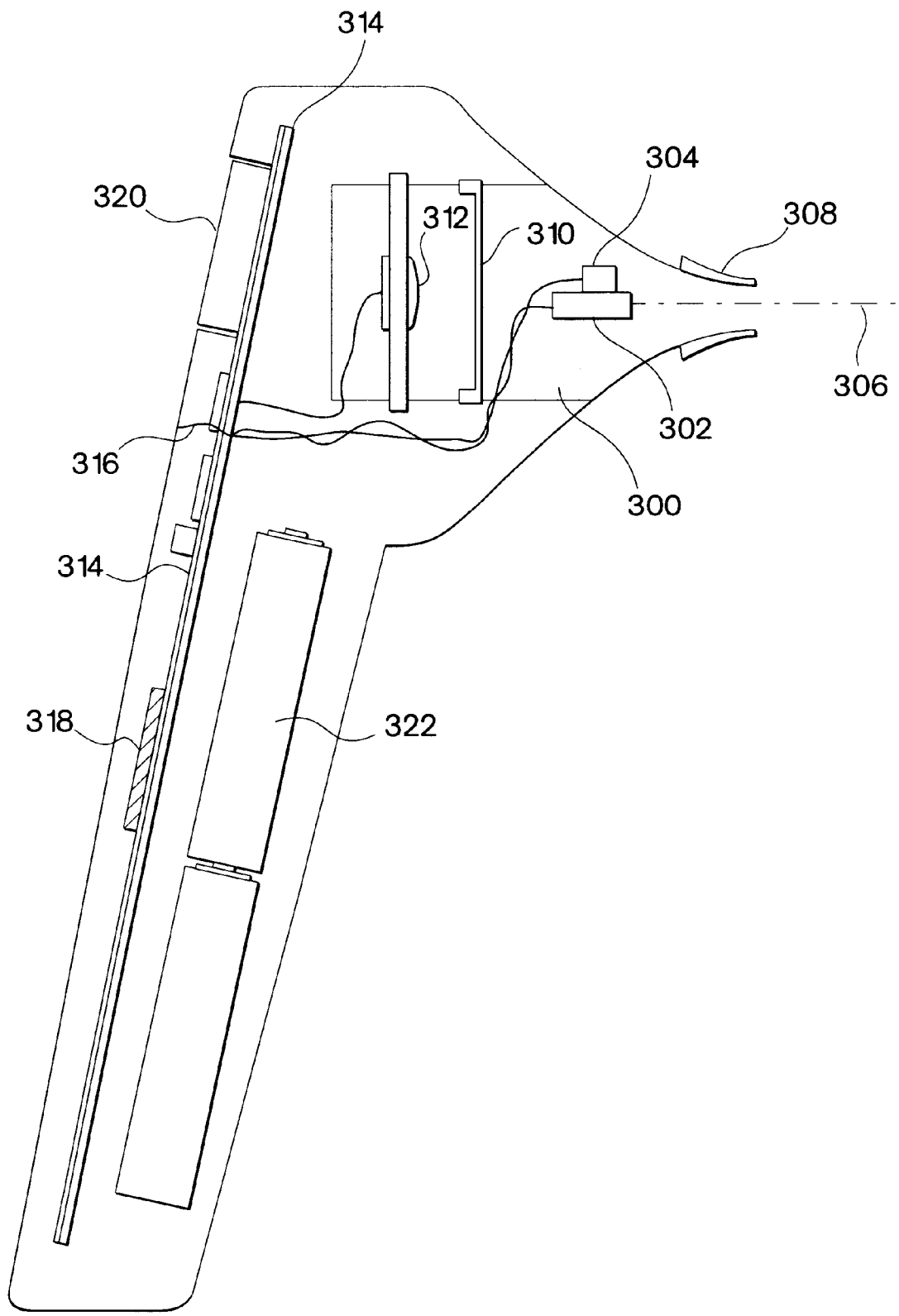
FIG. 8 is a diagram illustrating the physical layout of the microphone of the acoustic reflectometer and the radiation sensor within the acoustic chamber in one embodiment of the present invention.

The physical arrangement of the microphone and sensor within an acoustic chamber in a device will now be described in more detail in connection with FIG. 8. FIG. 8 shows a cross section of a device in one embodiment of the present invention. The device includes an acoustic chamber 300 in which a radiation sensor 302 and microphone 304 are disposed. The radiation sensor 302 is aligned with an axis 306 through the tip 308 of the device. An acoustic resistor 310 and speaker 312 generate the acoustic waves out of the device. The device also includes a printed circuit board 314 which contains analog circuitry 316 for processing and controlling the speaker, microphone and radiation sensor. The device may be powered by batteries 322. A microprocessor 318 is used to process these results and generate output to a user using the LCD display 320, in response to the user pressing an input button 324. Suitable designs for the LCD display include a display of temperature and a measure of the likelihood of fluid being present in the ear, such as described in the patents cited above. The device may be calibrated in the manner described in PCT Publication WO96/23293.

Figure 9:
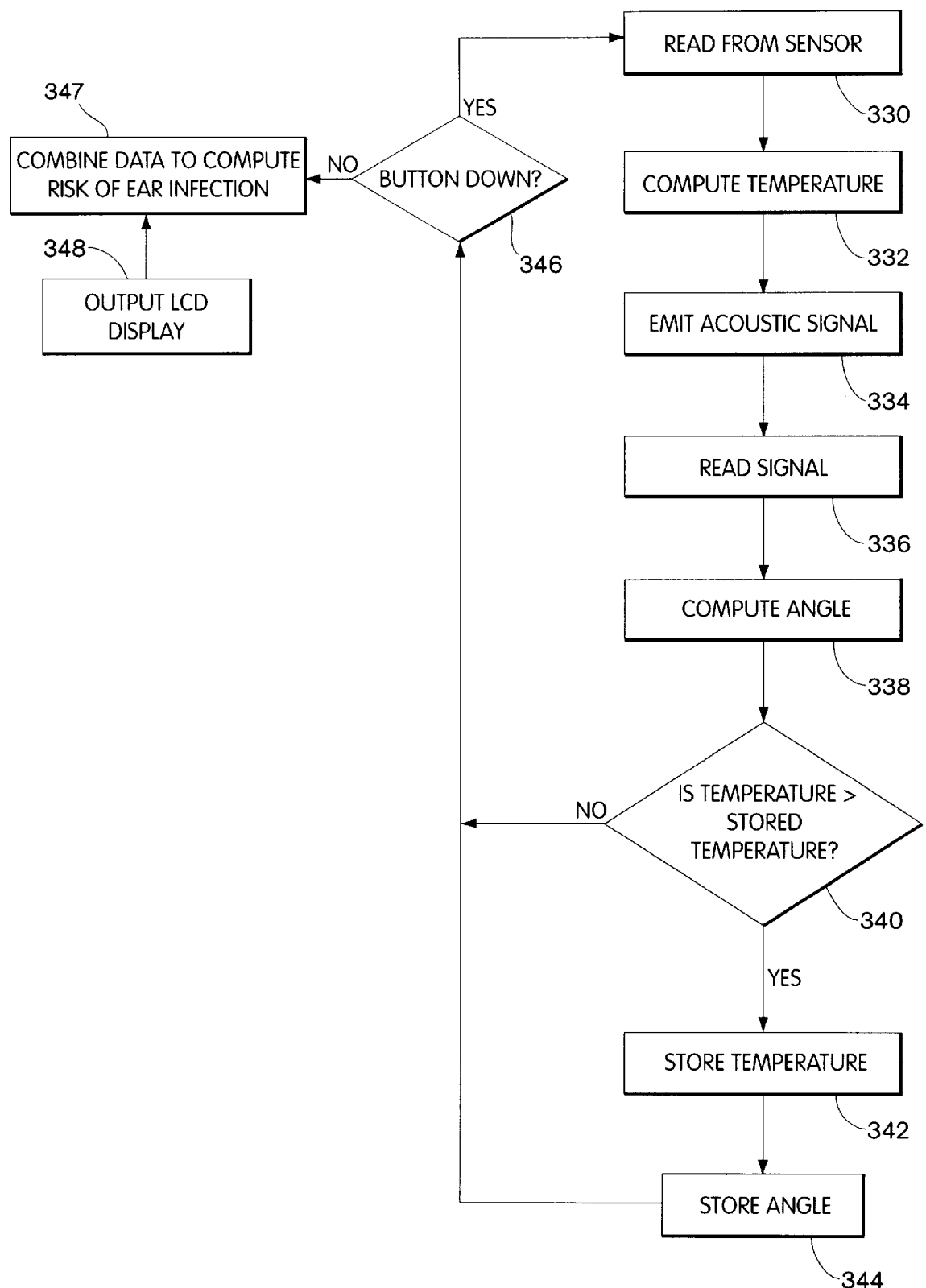
FIG. 9 is a flow chart describing how readings from the radiation sensor and microphone are coordinated to provide an output to a user.

FIG. 9 is a flow chart describing how the microprocessor controller 38 (FIG. 1) coordinates the reading of information from the microphone and radiation sensor to provide an output to the user. So long as the user is providing an input signal indicating a reading should be taken, for example by pressing the input button, data from the radiation sensor is read in step 330. The user should rotate the device with the tip against the opening to the ear canal while pressing the button. Any lobe of the ear also may be pulled lightly back to help align the device. An uncorrected temperature is then computed from the radiation sensor data using known techniques in step 332. The acoustic signal is also emitted in step 334 and a signal is read from the microphone in step 336. A measure of the likelihood of the presence of fluid is then determined in step 338. For example, this measure may be determined by computing the measure of the shape of the acoustic reflectance curve, or by measuring the peak of the acoustic reflectance curve. If the temperature computed in step 332 is greater than any stored temperature, as determined in step 340, the currently measured temperature is stored in step 342 and the computed acoustic reflectance measure is then also stored in step 344. Alternatively, step 340 could search for a minimized angle or peak value in the acoustic reflectance curve and store the corresponding temperature and angle or peak value in steps 342 and 344. If the user input signal still indicates a reading should be taken, as determined in step 346, the process of steps 330–344 is repeated. Otherwise, the resulting output is provided to the LCD display in step 348, possibly providing a corrected temperature as shown in U.S. Pat. No. 5,626,147.

The combination of a radiation thermometer and acoustic reflectometer improves the accuracy of the device with respect to the line of sight to the tympanic membrane, and provides enhanced diagnostic utility. The determination of the presence or absence of an abnormal temperature in conjunction with the determination of the likelihood of presence of fluid may assist a physician in the diagnosis of an acute otitis media with an effusion. In particular, an elevated temperature and the presence of fluid indicate a high risk of ear infection.

The measured temperature and the measure related to acoustic reflectance, such as an angle, may be displayed separately and/or may be combined to provide an additional diagnostic measure. In general, the more abnormal the temperature, the more certain a diagnosis of ear infection may be with the presence of fluid. This diagnostic measure may be computed in many ways, such as a look up table that maps ranges of temperature and acoustic reflectance to the likelihood that an ear infection is present.

In one embodiment, the device, under microprocessor control, measures ear temperature and detects the presence of middle ear fluid. The measurements are stored in a memory. Using the temperature and fluid data, the processor then uses a relational formula or a look-up table to determine the probability of ear infection. For example, as shown in FIG. 10, column 500 represents normal temperatures (e.g. <99° F.). Column 502 represents a slightly elevated temperature (e.g. 99° to 100° F.) and column 504 represents an elevated temperature (e.g. >100° F). Row 506 corresponds to normal acoustic reflectance. Row 508 corresponds to an increased possibility that fluid is present in the ear. Row 510 corresponds to acoustic reflectance which is highly likely to be indicative of the presence of fluid in the ear. As can be seen, an elevated temperature and increased likelihood of fluid being present in the ear very likely indicates acute otitis media, as shown at boxes F, H and I. Box A of the table indicates a healthy ear. The likelihood of ear infection is also low for boxes B, C and D. Otitis media with effusion is highly likely in box G and moderately likely in box D. Acute otitis media is moderately likely in box E. The correspondence of the boxes to the likelihood of ear infection being present is shown in FIG. 11. Similarly, such a table for fluid is shown in FIG. 12. Note that box D corresponds to a low likelihood of ear infection, but moderate likelihood of the presence of fluid. Similarly, while box G indicates a high likelihood of an effusion being present, such a result indicates only a moderate likelihood of an ear infection. Finally, box F, which indicates only a moderate likelihood of fluid being present, indicates a high likelihood of an ear infection being present. As a result, the information provided by this device would be different from a device that merely detects the likelihood of the presence of fluid.

There are numerous display formats ranging from quantitative numerical readings to ranges of risk level. For example, the ranges of risk level shown in FIGS. 11 and 12 could be displayed to a user. Alternatively, the absolute values of temperature and acoustic reflectance also could be displayed to the user.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims.

What is claimed is:

1. A medical instrument for analyzing an ear of a subject, comprising:
   an acoustic reflectometer comprising an acoustic transducer for generating acoustic waves at a plurality of frequencies and a microphone for receiving acoustic signals reflected from the ear to provide an output signal;
   a radiation sensor for detecting thermal radiation from the ear and providing a signal indicative thereof; and
   a controller connected to the acoustic reflectometer and radiation sensor.

2. The medical instrument of claim 1, further comprising:
   means for indicating to the user when both an elevated temperature and fluid are detected in the ear.

3. The medical instrument of claim 2, wherein the means for indicating includes:
   means for combining temperature and fluid information to provide an indication of a risk of ear infection.

4. A process for analyzing an ear of a subject, comprising the steps of:
   measuring acoustic reflectance from the ear and providing a signal indicative thereof;
   detecting thermal radiation from the ear and providing a signal indicative thereof; and
   providing a signal indicative of the measured acoustic reflectance and the detected thermal radiation.

5. The process of claim 4, wherein the step of measuring acoustic reflectance comprises the steps of:
   generating acoustic waves at a plurality of frequencies; and
   detecting acoustic signals reflected from the ear to provide the signal.

6. The process of claim 4, further comprising the step of:
   generating an indication to the user when both an elevated temperature and fluid are detected in the ear.

7. The process of claim 4, further comprising the step of:
   combining temperature and fluid information to provide an indication of a risk of ear infection.

* * * * *